(12) United States Patent
Nakahata et al.

(10) Patent No.: US 7,569,040 B2
(45) Date of Patent: *Aug. 4, 2009

(54) ABSORBENT ARTICLE HAVING STRETCHABLE FASTENING MEMBER

(75) Inventors: Hiroshi Nakahata, Kobe Hyogo (JP); Yasuhisa Minemoto, Akashi Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/799,015

(22) Filed: Apr. 30, 2007

(65) Prior Publication Data

US 2007/0203470 A1     Aug. 30, 2007

(51) Int. Cl.
*A61F 13/15* (2006.01)
(52) U.S. Cl. ............... 604/391; 604/385.11; 604/385.16
(58) Field of Classification Search ............. 604/385.11, 604/385.16, 389–391
See application file for complete search history.

(56) References Cited

U.S. PATENT DOCUMENTS

| | | | |
|---|---|---|---|
| 4,695,278 A | | 9/1987 | Lawson |
| 4,704,115 A | | 11/1987 | Buell |
| 4,795,454 A | | 1/1989 | Dragoo |
| 4,909,803 A | | 3/1990 | Aziz et al. |
| 5,464,401 A | * | 11/1995 | Hasse et al. ............. 604/385.25 |
| 5,624,428 A | * | 4/1997 | Sauer ......................... 604/391 |
| 5,662,638 A | * | 9/1997 | Johnson et al. ............. 604/386 |
| 5,685,873 A | * | 11/1997 | Bruemmer ............. 604/385.24 |
| 7,217,262 B2 | * | 5/2007 | Nakahata et al. ............ 604/391 |
| 2002/0099352 A1 | * | 7/2002 | Heden et al. ................. 604/387 |
| 2002/0165514 A1 | * | 11/2002 | Datta et al. ............. 604/385.11 |
| 2004/0236301 A1 | * | 11/2004 | Wendelstorf et al. ........ 604/387 |

FOREIGN PATENT DOCUMENTS

EP         832205 A1     4/1998

* cited by examiner

*Primary Examiner*—Tatyana Zalukaeva
*Assistant Examiner*—Lynne Anderson
(74) *Attorney, Agent, or Firm*—Thibault Fayette

(57) ABSTRACT

An absorbent article comprising a stretchable fastening member is disclosed. The absorbent article comprises a chassis and a stretchable fastening member. The chassis extends longitudinally and laterally and comprises a liquid pervious topsheet, a liquid impervious backsheet and an absorbent core disposed therebetween. The stretchable fastening member comprises a fixed portion permanently joined to the chassis, a distal portion provided with a fastening material and a stretchable panel positioned between the fixed portion and the distal portion. The stretchable fastening member is joined to the chassis such that the distal portion is positioned laterally outwardly from the fixed portion in the flat-out configuration of the stretchable fastening member. The stretchable panel of the stretchable fastening member comprises a first stretchable zone and a second stretchable zone disposed in the lateral direction. The first stretchable zone is capable of providing extensibility upon an initially applied extension force. Extensibility of the second stretchable zone is restricted by a restriction means until the restriction means is inactivated, and the restriction means is inactivated upon a further applied extension force such that the second stretchable zone provides an additional extensibility to reduce a stress developed in the stretchable panel.

8 Claims, 11 Drawing Sheets

ABSORBENT ARTICLE HAVING STRETCHABLE FASTENING MEMBER

CROSS REFERENCE TO RELATED APPLICATION

This application claims the benefit of prior U.S. application Ser. No. 10/733,620, filed Dec. 11, 2003, which claims the benefit of U.S. Provisional Application No. 60/440,919, filed Jan. 17, 2003, the substances of which are incorporated herein by reference.

TECHNICAL FIELD

The present invention relates to an absorbent article comprising a stretchable fastening member. More specifically, the present invention relates to an absorbent article comprising a stretchable fastening member comprising a first stretchable zone being capable of providing extensibility upon an initially applied elongation force and a second stretchable zone to provide an additional extensibility upon a further applied elongation force to reduce a stress developed in the stretchable fastening member.

BACKGROUND

Fastening systems are widely known and widely used. Disposable absorbent articles are one example which is provided with fastening systems. The fastening systems provided on disposable absorbent articles are to form a closure of so-called open type absorbent articles (e.g., taped diaper) when in use or to adjust the dimension of the waist circumference of so-called pull-on type absorbent articles (e.g., pull-on diaper). In conventional arrangement of fastening systems on disposable diapers, the fastening member of the fastening system is provided to extend in the direction parallel to the lateral direction of the diaper such that the fastening member is pulled in the lateral direction for fastening the diaper and for forming a defined dimension of the waist opening. This provides a lateral tensioning force to keep the diaper in the abdominal region of the wearer.

Fastening members provided with stretchability have been also well known and used in absorbent articles such as diapers. The use of stretchable fastening member allows the diaper to accommodate wide ranges of wearer's waist circumference. However, the stress developed in the stretchable fastening member is very different depending on the circumference size of the wearer's waist. For example, the stretchable fastening member generates higher stress to cause excess forces on the wearer's body when the diaper having the stretchable fastening member is applied to a relatively big wearer than when the same diaper is applied to a relatively small wearer. Such excess forces cause skin problems such as red marking. In contrast, the stretchable fastening member generates only smaller stress to cause insufficient force on the wearer's body when the diaper is applied to a relatively small wearer than when the same diaper is applied to a relatively big wearer. Such insufficient force causes fitment problems of the diaper such as sagging. These problems are due to a typical behavior of the conventional stretchable fastening member in which stress developed in the stretchable fastening member simply continuously increases as strain of the stretchable fastening member increases.

European Patent publication EP 0 838 205 A3 published on May 31, 2002 discloses a disposable absorbent garment including a pair of differently stretchable ear members. Each differently stretchable ear member comprises a stretchable inner ear portion having a first stretchable characteristic and a stretchable outer ear portion having a second stretchable characteristic. It is stated that each stretchable outer ear portion preferably has a lower tension than stretchable inner ear portions, and each stretchable outer ear portion preferably has an elongation equal to or greater than that of a stretchable inner ear portion. Because stretchable inner ear portions are used primarily to fit and support absorbent article on the wearer, stretchable outer ear portions may have a lower tension so that they easily stretch to permit snap fastener to be closed without adding additional tension or stretch to inner ear portions that provide the proper fit and support. Thus, the stretchable inner ear portion and the stretchable outer ear portion may take a different stress-strain curve. However, the stress developed in such a stretchable ear member continuously increases as the strain of the stretchable ear member increases The stretchable ear member of the art can not reduce the stress developed in the stretchable ear member as it is stretched. Therefore, the stretchable ear member generates higher stress to cause excess forces on the wearer's body when the diaper is applied to a relatively big wearer. On the contrary, the stretchable ear member only generates stress to cause insufficient force on the wearer's body when the diaper is applied to a relatively small wearer. Thus, the stretchable ear member of the art limits the range of wearer's waist circumference size in which the diaper is comfortably applicable to the wearer.

Based on the foregoing, there is a need for an absorbent article having a stretchable fastening member being capable of controlling stress over the wide range of strain to accommodate wide ranges of wearer's waist circumference. None of the existing absorbent articles provides all of the advantages and benefits of the present invention.

SUMMARY

The present invention is directed to an absorbent article comprising a stretchable fastening member. The absorbent article comprises a chassis and a stretchable fastening member. The chassis extends longitudinally and laterally and comprises a liquid pervious topsheet, a liquid impervious backsheet and an absorbent core disposed therebetween. The stretchable fastening member comprises a fixed portion permanently joined to the chassis, a distal portion provided with a fastening material and a stretchable panel positioned between the fixed portion and the distal portion. The stretchable fastening member is joined to the chassis such that the distal portion is positioned laterally outwardly from the fixed portion in the flat-out configuration of the stretchable fastening member. The stretchable panel of the stretchable fastening member comprises a first stretchable zone and a second stretchable zone disposed in the lateral direction. The first stretchable zone is capable of providing extensibility upon an initially applied extension force. Extensibility of the second stretchable zone is restricted by a restriction means until the restriction means is inactivated, and the restriction means is inactivated upon a further applied extension force such that the second stretchable zone provides an additional extensibility to reduce a stress developed in the stretchable panel.

BRIEF DESCRIPTION OF THE DRAWINGS

While the specification concludes with claims particularly pointing out and distinctly claiming the invention, it is believed that the present invention will be better understood from the following description of preferred embodiments taken in conjunction with the accompanying drawings in which:

DETAILED DESCRIPTION

As used herein, the term "comprising" means that other steps and other ingredients which do not affect the end result can be added. This term encompasses the terms "consisting of" and "consisting essentially of."

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, and the like. The term "longitudinal", as used herein, refers to a line, axis or direction in the plane of the absorbent article that is generally aligned with (e.g., approximately parallel to) a vertical plane which bisects a standing wearer into left and right body halves when the absorbent article is worn. The terms "transverse" or "lateral" used herein, are interchangeable, and refer to a line, axis or direction which lies within the plane of the absorbent article that is generally perpendicular to the longitudinal direction.

Figure 1:
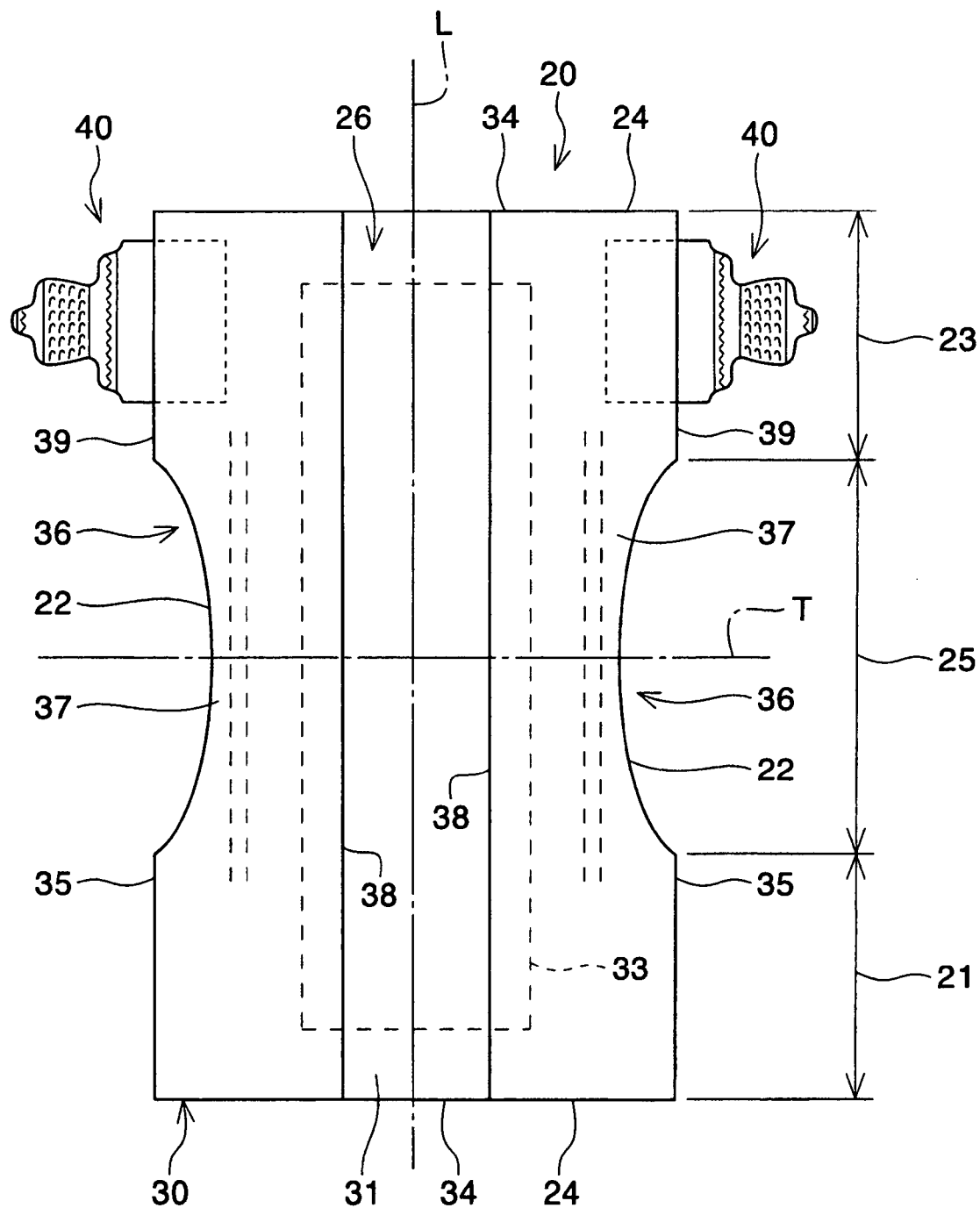
FIG. 1 is a top plan view of one embodiment of an absorbent article having a stretchable fastening member with a restriction means.
Figure 2:
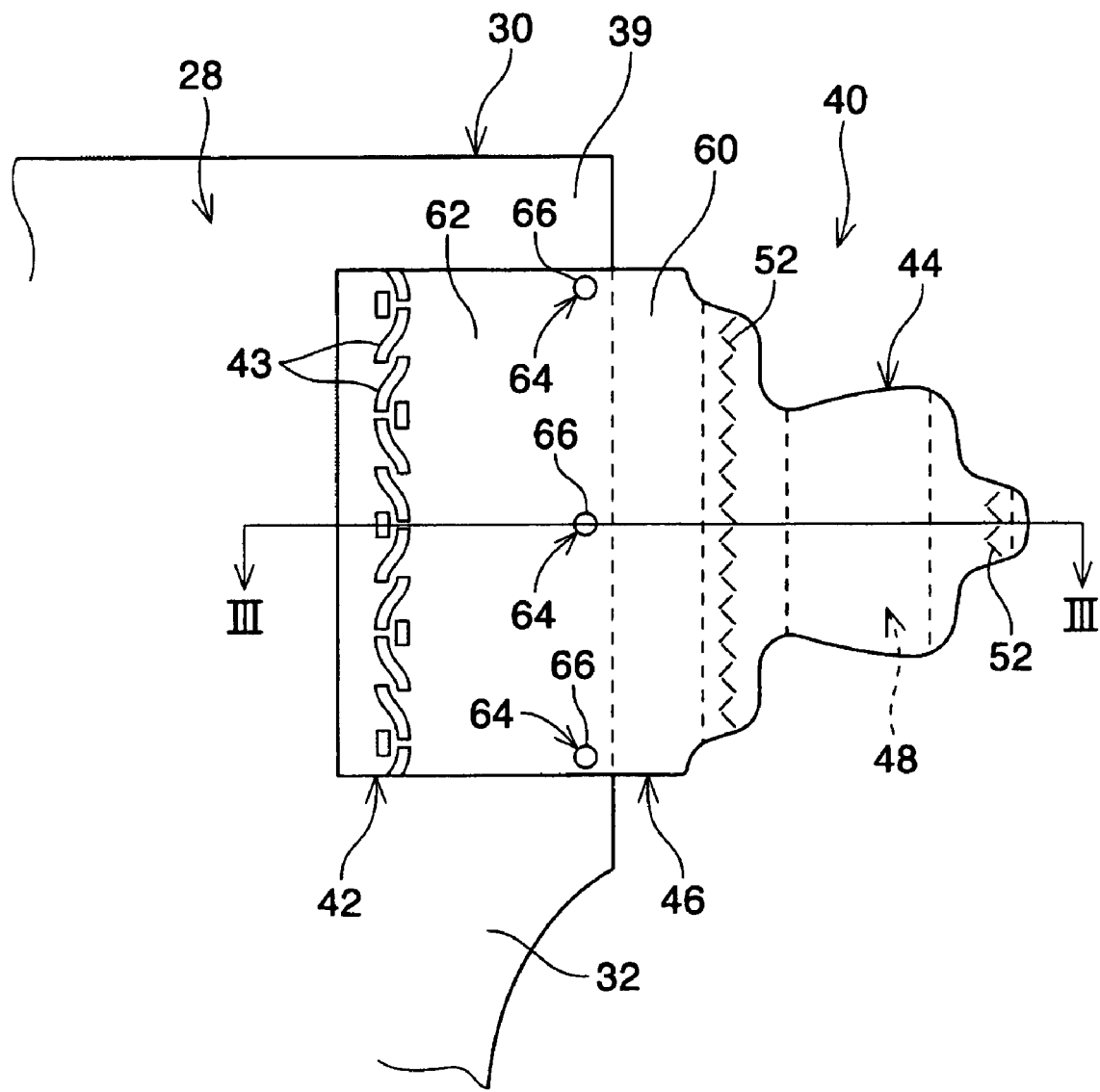
FIG. 2 is a partially enlarged top plan view of the stretchable fastening member in its flat-out configuration.
Figure 3:
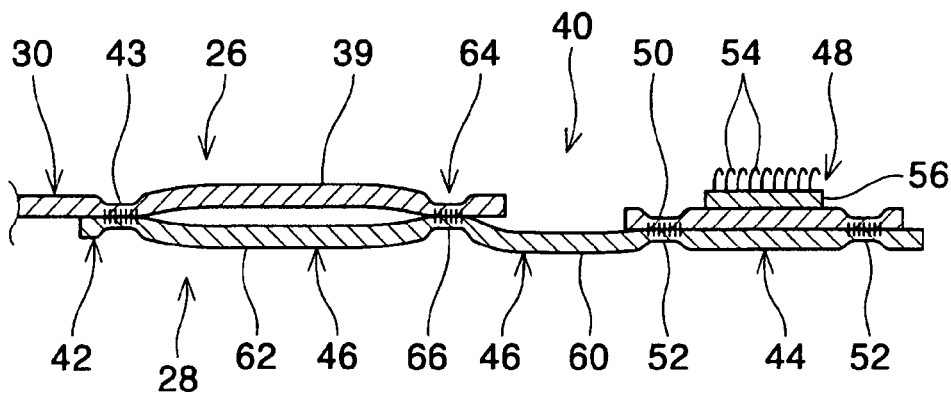
FIG. 3 is a cross-sectional view taken along the line III-III of FIG. 2.

FIG. 1 is a top plan view of the diaper 20 in its flat-out configuration. The diaper 20 comprises a chassis 30 and a stretchable fastening member 40. Referring to FIG. 2 showing a partially enlarged top plan view of the stretchable fastening member in its flat-out configuration and FIG. 3 showing a cross-sectional view taken along the line III-III of FIG. 2, the diaper 20 has a wearer facing surface 26, an opposite outer surface 28, a longitudinal centerline L, and a lateral centerline T. The diaper 20 also has longitudinal side edges 22 which run generally in the longitudinal direction of the diaper and lateral end edges 24 which run between the longitudinal side edges 22 generally in the lateral direction of the diaper 20. The periphery of the diaper 20 is defined by the longitudinal side edges 22 and the lateral end edges 24. The diaper 20 further has a front waist region 21, a back waist region 23 and a crotch region 25 disposed between the front waist region 21 and the back waist region 23.

The diaper 20 comprises a chassis 30 and a stretchable fastening member 40 joined to the chassis 30. The chassis 30 has a generally rectangle shape in its flat-out configuration and extends longitudinally and laterally. The chassis 30 comprises a liquid pervious topsheet 31; a liquid impervious backsheet 32; an absorbent core 33 which is disposed between at least a portion of the topsheet 31 and the backsheet 32; and a side flap 39 extending laterally outwardly from the absorbent core 33. The chassis 30 has lateral end edges 34 and longitudinal side edges 35. The lateral end edge 34 of the chassis 30 generally defines the lateral end edge 24 of the diaper 20. The longitudinal side edge 35 of the chassis 30 generally defines the longitudinal side edge 22 of the diaper 20. The chassis 30 may further comprise a leg cuff 36 comprising an elasticized gasketing cuff 37 disposed adjacent to the longitudinal side edge 22 in the crotch region 25 and an elasticized barrier cuff 38. The chassis 30 may also comprise an elastic waist feature (not shown in Figures).

The liquid pervious topsheet 31 is preferably positioned adjacent the body-facing surface of the absorbent core 33 and may be joined thereto and/or to the backsheet 32 by any attachment means known in the art. The topsheet 31 is preferably compliant, soft feeling, and non-irritating to the wearer's skin. Further, at least a portion of the topsheet 31 is liquid pervious, permitting liquid to readily penetrate through its thickness. A suitable topsheet 31 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 31 is made of a hydrophobic material or is treated to be hydrophobic in order to isolate the wearer's skin from liquids contained in the absorbent core 33. If the topsheet 31 is made of a hydrophobic material, preferably at least the upper surface of the topsheet 31 is treated to be hydrophilic so that liquids will transfer through the topsheet more rapidly.

The liquid impervious backsheet 32 is generally that portion of the diaper 20 positioned adjacent the garment-facing surface of the absorbent core 33. The backsheet 32 prevents the exudates absorbed and contained therein from soiling articles that may contact the diaper 20, such as bedsheets and undergarments. In preferred embodiments, the backsheet 32 is impervious to liquids (e.g., urine) and comprises a thin plastic film. Suitable backsheet materials may include breathable materials that permit vapors to escape from the diaper 20 while still preventing exudates from passing through the backsheet 32. Exemplary breathable materials may include materials such as woven webs, nonwoven webs, composite materials such as film-coated nonwoven webs, and microporous films. The backsheet 32 may be covered by a woven or a nonwoven to impart more cloth-like appearance to the diaper. Preferably a nonwoven is provided to cover the entirety of the backsheet 32.

The absorbent core 33 may comprise any absorbent material that is generally compressible, conformable, non-irritating to the wearer's skin, and capable of absorbing and retaining liquids such as urine and other certain body exudates. The absorbent core 33 can be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In any case all or a portion of the core may include slits which allow the core to form openings when stretched into which fecal mater can flow. The configuration and construction of the absorbent core 33 may also be varied (e.g., the absorbent core(s) or other absorbent structure (s) may have varying caliper zones, a hydrophilic gradient, a superabsorbent gradient, or lower average density and lower average basis weight acquisition zones; or may comprise one or more layers or structures). However, the total absorbent capacity of the absorbent core 33 should be compatible with the design loading and the intended use of the diaper 20.

The side flap 39 is a part of the chassis 30 along the longitudinal side edge 35 of the chassis 30 which extends laterally outwardly from the absorbent core 33. The side flap 39 may be formed with at least one element constituting the chassis 30, such as an extension of topsheet, an extension of backsheet (either of a backsheet film or a nonwoven outer cover), an extension of a leg cuff, or a combination thereof. Alternatively, the side flap 39 may be formed with a separate element joined to other elements of the chassis, such as a topsheet, a backsheet, and/or a leg cuff.

The leg cuff 36 provides improved containment of liquids and other body exudates. The leg cuff 36 may comprise several different embodiments for reducing the leakage of body exudates in the leg regions. Such embodiments are disclosed in, e.g., U.S. Pat. No. 4,909,803 issued to Aziz et al. on Mar. 20, 1990; U.S. Pat. No. 4,695,278 issued to Lawson on Sep. 22, 1987; U.S. Pat. No. 4,795,454 issued to Dragoo on Jan. 3, 1989; and U.S. Pat. No. 4,704,115 issued to Buell on Nov. 3, 1987; each of which are incorporated herein by reference. It is preferred that the leg cuff 36 comprises at least an elasticized barrier cuff 38 such as described in the above-referenced U.S. Pat. No. 4,909,803. The leg cuff 36 also comprises an elasticized gasketing cuff 37 with one or more elastic strands, positioned outboard of the barrier cuff such as described in the above-referred U.S. Pat. No. 4,695,278.

The stretchable fastening member 40 is provided on the back waist region 23 of the diaper 20 and is joined to the chassis 30. The stretchable fastening member 40 comprises a fixed portion 42, a distal portion 44 and a stretchable panel 46. The fixed portion 42 is permanently joined to the side flap 39 of the chassis 30 at bonding sites 43 by any known means such as adhesives, heat bonding, pressure bonding, heat and pressure bonding, ultrasonic bonding, or any combination thereof. The distal portion 44 is provided with a fastening material 48 used to form a closure of the diaper 20 with a landing zone member (not shown in the drawings) which is provided on the front waist region 21 of the diaper 20. The stretchable panel 46 is positioned laterally between the fixed portion 42 and the distal portion 44. The stretchable panel 46 provides stretchability upon an applied extension force generated by pulling the stretchable fastening member 40. As shown in FIG. 2, the distal portion 44 is positioned laterally outwardly from the fixed portion 42 through the stretchable panel 46 in the flat-out configuration of the stretchable fastening member 40. The fixed portion 42, the distal portion 44 and the stretchable panel 46 may be formed with an integral material or may be formed with separate materials joined to each other. In the embodiment shown in FIGS. 2 and 3, the fixed portion 42 and the distal portion 44 are formed with an extension of the stretchable panel 46.

The distal portion 44 of the stretchable fastening member 40 is provided with a fastening material 48. The fastening material 48 is joined to the extension of the stretchable panel 46 through an intermediate sheet 50 which may comprise a plastic film. However, the fastening material 48 may be directly joined onto the extension of the stretchable panel 46. The fastening material 48 is joined to the extension of the stretchable panel 46 by any known means. In the embodiment shown in FIGS. 2 and 3, the fastening material 48 is joined to the intermediate plastic film 50 by adhesives and the intermediate plastic film is joined to the extension of the stretchable panel 46 by pressure and heat bonding means at the bonding sites 52. The fastening material 48 is intended to provide a fastening means for engaging the landing zone member so as to provide a secure side closure for the diaper 20. In the embodiment shown in FIGS. 2 and 3, the fastening material 48 comprises a hook fastening material comprising a plurality of hooks 54 and the base substrate 56 to support the hooks 54. It should be understood that the use of the term "hook" should be non-limiting in the sense that the engaging elements may comprise any shapes as are known in the art so long as they are adapted to engage a complementary landing zone member. Alternatively, the fastening material 48 may be adhesives or a combination of adhesives and hook fastening materials.

The stretchable panel 46 may comprise any material exhibiting stretchability including a plastic film, woven, or nonwoven webs of natural fibers (e.g., wood or cotton fibers), synthetic fibers (e.g., polyester or polypropylene fibers), elastomeric adhesives or a combination of natural and synthetic fibers or may comprise any combination of materials thereof. The stretchable panel 46 is preferably compliant, soft feeling, and non-irritating to the wearer's skin as the stretchable panel 46 may touch the wearer's skin when in use. Further, at least a portion of the stretchable panel 46 may be vapor pervious, permitting vapor to readily penetrate through its thickness. Suitable stretchable panel materials include a stretchable laminate comprising a stretchable plastic film and nonwoven layers laminated on the plastic film such that the stretchable plastic film is interposed between the nonwoven layers.

Figure 4:
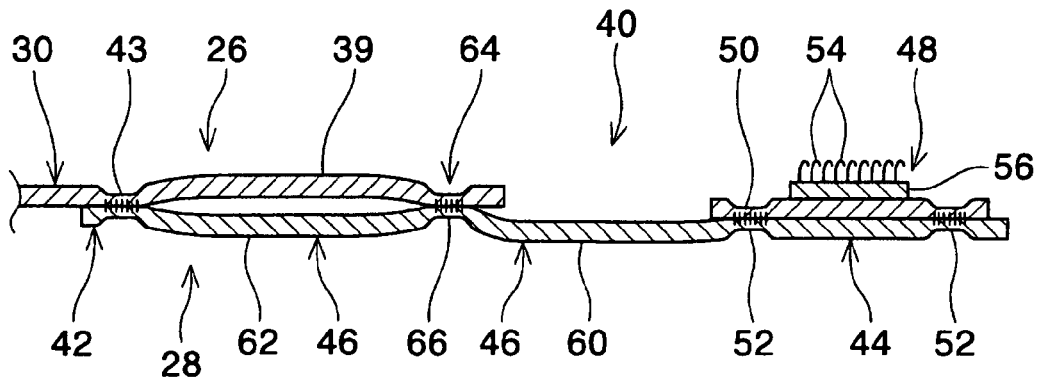
FIG. 4 is a cross-sectional view taken along the line III-III of FIG. 2 in which the first stretchable zone is stretched.
Figure 5:
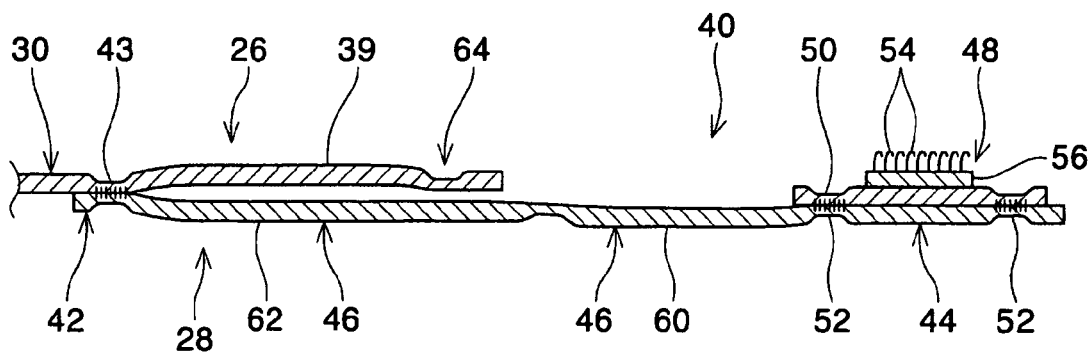
FIG. 5 is a cross-section view taken along the line III-III of FIG. 2 in which the restriction means is inactivated and the stretchable fastening member is stretched.

The stretchable panel 46 extends laterally outwardly from the fixed potion 42 and provides stretchability between the fixed portion 42 and the distal portion 44. The stretchable panel 46 is extensible in the lateral direction. The stretchable panel 46 comprises a first stretchable zone 60 and a second stretchable zone 62 which is disposed laterally inwardly from the first stretchable zone 60. Therefore, the first stretchable zone 60 and the second stretchable zone 62 are positioned adjacent to the distal portion 44 and the fixed portion 42, respectively. The first stretchable zone 60 is capable of providing extensibility upon an initially applied extension force generated by pulling the stretchable fastening member 40. However, extensibility of the second stretchable zone 62 is restricted by a restriction means 64 until the restriction means 64 is inactivated. Therefore, the only first stretchable zone 60 provides extensibility upon an initially applied extension force and the extensibility of the second stretchable zone 62 is preserved until the restriction means 64 is inactivated (refer to FIG. 4). When the restriction means 64 is inactivated upon a further applied extension force as shown in FIG. 5, the second stretchable zone 62 is capable of providing an additional extensibility to reduce a stress developed in the stretchable panel 46 (i.e., stress developed in the first stretchable zone 62). The term "inactivated" used herein means that the restriction means loses at least a part of restriction function so that at least a part of the second stretchable zone is capable of providing an extensibility. Therefore, even though the restriction means is inactivated, the restriction means may still provide a part of restriction function while it does not provide a full restriction function as initially installed. The term "full restriction function as initially installed" means the restriction function of the restriction means which a fresh diaper taken out from a new package exhibits.

Figure 6:
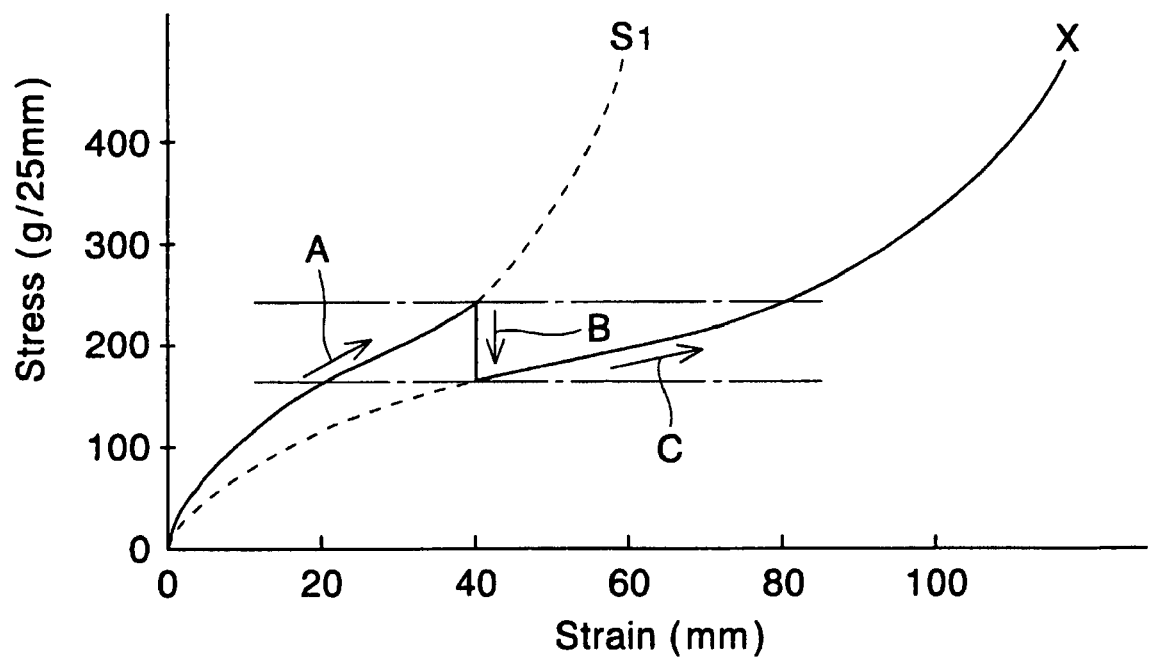
FIG. 6 is a graph showing the stress-strain curve of the stretchable fastening member shown in FIG. 2.

FIG. 6 shows a stress-strain curve of the entire stretchable panel 46 combining the first stretchable zone 60 and the second stretchable zone 62. In FIG. 6, the curve S1 exhibits a stress-strain curve of the first stretchable zone 60. The curve X exhibits a stress-strain curve of the entire stretchable panel 46. The profile difference between the curve S1 and the curve X is due to the lateral width difference of the material which provides stretchability. As shown, the first stretchable zone 60 (curve S1) provides relatively higher stress than the entire stretchable panel 46 (curve X) at low strain zone (e.g., at the strain between about 20 mm and about 40 mm) to generate force to sustain the diaper 20 on the wearer. However, the first stretchable zone 60 rapidly increases the stress at the high strain zone (e.g., at the strain zone higher than about 40 mm) to cause excess force on the wearer's skin. On the contrary, the entire stretchable panel 46 would provide an appropriate stress at the high strain zone to generate force to sustain the diaper 20 on the wearer without causing excess force on the wearer's skin. Therefore, it is desirable to be able to use the first stretchable zone 60 exhibiting the curve S1 at the low strain zone and the entire stretchable panel 46 exhibiting the curve X at the high strain zone.

In the present invention, the restriction means 64 withstands the initially applied extension force to restrict the stretchability of the second stretchable zone 62 until the restriction means 64 is inactivated. Therefore, the first stretchable zone 60 is stretched along the arrow A on the curve S1 upon an initially applied extension force generated by pulling the stretchable fastening member 40 and the stress-strain curve of the stretchable fastening member 40 follows the curve S1. When the stretchable fastening member 40 is stretched by a further applied extension force, the restriction means 64 is inactivated and the second stretchable zone 62 provides an additional extensibility to reduce the stress developed in the stretchable panel 46 (i.e., the stress developed in the first stretchable zone 60) as shown by the arrow B in FIG. 6. In the embodiment shown in FIG. 6, the restriction means 64 is inactivated at the strain of about 40 mm. Then, the entire stretchable panel 46 is stretched along the arrow C on the curve X upon a further applied extension force and the stretchable fastening member 40 follows the curve X In the embodiment shown in FIG. 6, if the only first stretchable zone 62 is used for the stretchable fastening member 40, the strain range is limited to between about 17 mm and about 40 mm to obtain the stress of between about 150 g/25 mm and about 250 g/25 mm. If the entire stretchable panel 46 is used for the stretchable fastening member 40, the strain range is limited to between about 40 mm and about 80 mm to obtain the same range. However, the present invention allows to utilize the strain range of between about 17 mm and about 80 mm to obtain the same range. Thus, the stretchable fastening member 40 of the present invention provides a relatively constant stress over the wide range of strain to accommodate wide ranges of wearer's waist circumference without causing skin problems by excess force and sagging problems by insufficient force. While the restriction means 64 is inactivated by an applied extension force to pull the stretchable fastening member 40, it is obvious that the restriction means 64 may be inactivated by the user of the diaper before application of the diaper 20 to the wearer if the diaper is used for a relatively big wearer. It is preferable that the restriction means 64 is inactivated before the stretchable fastening member 40 generates the stress to cause an excess force on the wearer's skin. Therefore, the restriction means 64 is preferably inactivated when the applied extension force is not more than 350 g/25 mm. The restriction means 64 is also preferably inactivated when the applied extension force is not less than 150 g/25 mm such that the restriction means withstands at least an initially applied extension force.

The restriction means 64 in the embodiment shown in FIGS. 2 and 3 comprises a bonding means 66 to detachably join a portion of the stretchable panel 46 to the side flap 39 of the chassis 30. The bonding means 66 is provided in the configuration where the stretchable panel 46 is unfolded and superposed on the side flap 39. The bonding means 66 is disposed between the fixed portion 42 and the distal portion 44. The restriction means 64 shown in FIG. 2 comprises three spots of bonding means 66 comprising a waist bonding means, a leg bonding means and a central bonding means between the waist and leg bonding means such that thee bonging means align in the longitudinal direction. If desired, the central bonding means may be removed in the embodiment shown in FIG. 2. The bonding means 66 virtually divides the stretchable panel 46 at the line connecting the three bonding means 66 to provide the first stretchable zone 60 extending between the distal portion 44 and the bonding means 66 and the second stretchable zone 62 extending between the fixed portion 42 and the bonding means 66. The bonding means 66 restricts the majority of stretchability of the second stretchable zone 62. Alternatively, the bonding means 66 may comprise four or more of bonding spots or may comprise a continuous bonding line to further restrict the stretchability of the second stretchable zone 62. The side flap 39 is preferably less stretchable than the stretchable panel 46, especially than the second stretchable zone 62, in order to restrict extensibility of the second stretchable zone 62. It is further preferable that the side flap 39 is non-stretchable for the same purpose.

While the bonding means may be formed with any known materials or methods such as adhesives, heat bonding, pressure bonding, heat and pressure bonding, ultrasonic bonding, or any combination thereof, the bonding strength of the bonding means 66 is selected so that the bonding means 66 withstands an initially applied extension force to maintain joint of the stretchable panel 46 to the side flap 39, but is inactivated upon a further applied extension force to detach the stretchable panel 46 from the side flap 39. In the embodiment shown in FIGS. 2 and 3, the bonding means 66 is formed by applying heat and pressure. The heat and pressure locally melts the materials of the stretchable panel 46 and the side flap 39 to form a fragile bonding site as shown in FIG. 3. The bonding strength of the bonding means 66 can be adjusted by changing the temperature and pressure. Alternatively, the bonding means 66 is formed with adhesives and the bonding strength of the bonding means can be adjusted by changing the amount of adhesives used.

Figure 7:
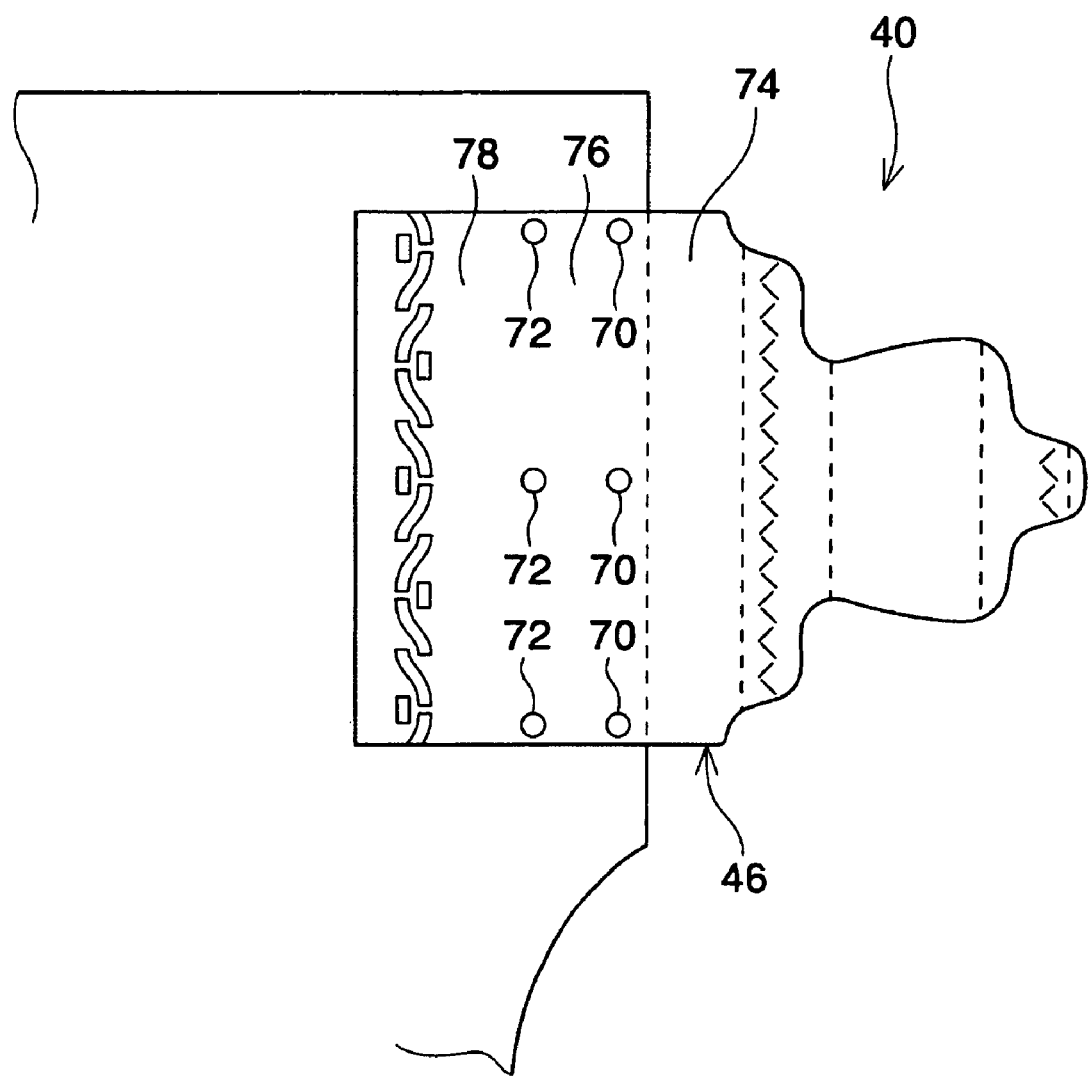
FIG. 7 is a first alternative embodiment of the stretchable fastening member with a restriction means.

Many alternatives are possible in forming a stretchable fastening member of the present invention while only representative examples are described below. FIG. 7 shows an alternative embodiment of a stretchable fastening member 40. The stretchable fastening member 40 shown in FIG. 7 comprises two sets of restriction means; first restriction means 70 and second restriction means 72. If desired, the stretchable fastening member 40 may comprise three or more sets of restriction means disposed in the lateral direction. Each set of restriction means may comprise three bonding means disposed in the longitudinal direction. The stretchable panel 46 comprises a first stretchable zone 74, a second stretchable zone 76 and a third stretchable zone 78. The first restriction means 70 virtually divides the stretchable panel 46 into the first stretchable zone 74 and the second stretchable zone 76 in the longitudinal direction. The second restriction means 72 virtually divides the stretchable panel 46 into the first stretchable zone 76 and the second stretchable zone 78 in the longitudinal direction.

Figure 8:
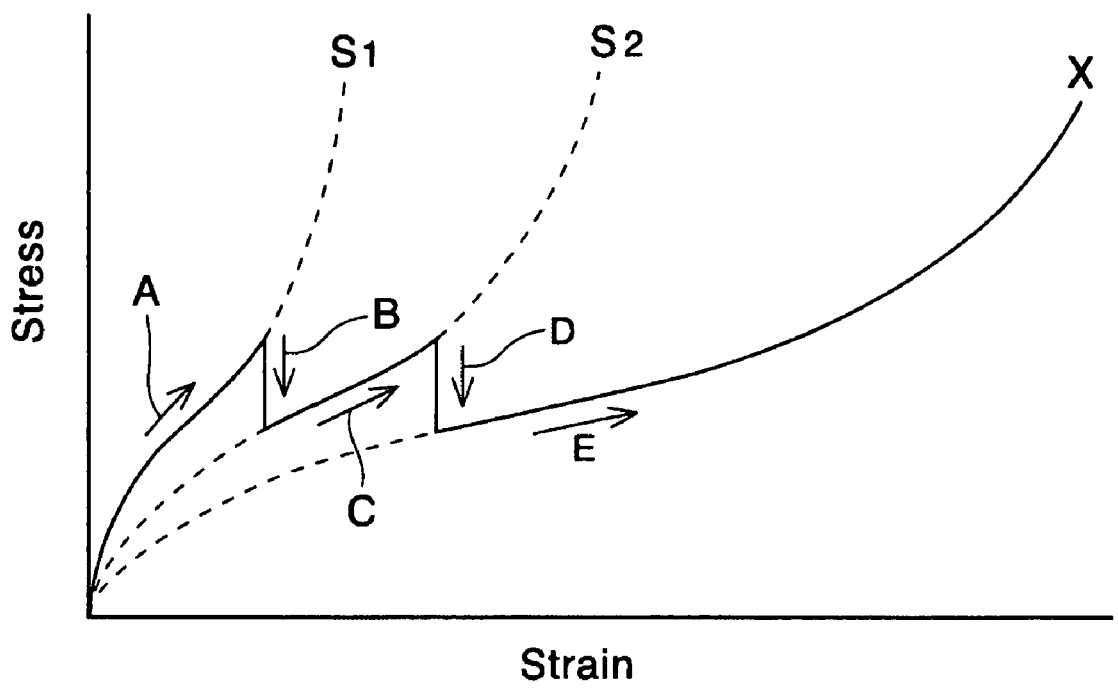
FIG. 8 is a graph showing the stress-strain curve of the stretchable fastening member shown in FIG. 7.

FIG. 8 shows a stress-strain curve of the entire stretchable panel 46 combining the first stretchable zone 74, the second stretchable zone 76 and the third stretchable zone 78. In FIG. 8, the curve S1 exhibits a stress-strain curve of the first stretchable zone 74. The curve S2 exhibits a stress-strain curve of a combined zone of the first stretchable zone 74 and the second stretchable zone 76. The curve X exhibits a stress-strain curve of the entire stretchable panel 46. The first restriction means 70 withstands the initially applied extension force to restrict the stretchability of the second stretchable zone 62 and the third stretchable zone 78 until the first restriction means 70 is inactivated. Therefore, the first stretchable zone 74 is stretched along the arrow A on the curve S1 upon an initially applied extension force generated by pulling the stretchable fastening member 40 and the stress-strain curve of the stretchable fastening member 40 follows the curve S1. When the stretchable fastening member 40 is stretched by a further applied extension force, the first restriction means 70 is inactivated and the second stretchable zone 76 provides an additional extensibility to reduce the stress developed in the stretchable panel 46 (i.e., the stress developed in the first stretchable zone 74) as shown by the arrow B in FIG. 8. Then, the combined zone of the first stretchable zone 74 and the second stretchable zone 76 is stretched along the arrow C on the curve S2 upon a further applied elongation and the stretchable fastening member 40 follows the curve S2. The second restriction means 72 withstands the further applied extension force to restrict the stretchability of the third stretchable zone 78. When the stretchable fastening member 40 is stretched by a further applied extension force, the second restriction means 72 is inactivated and the third stretchable zone 78 provides an additional extensibility to reduce the stress developed in the stretchable panel 46 as shown by the arrow D in FIG. 8. Then, the entire stretchable panel 46 is stretched along the arrow E on the curve X upon a further applied extension force and the stretchable fastening member 40 follows the curve X.

Figure 9:
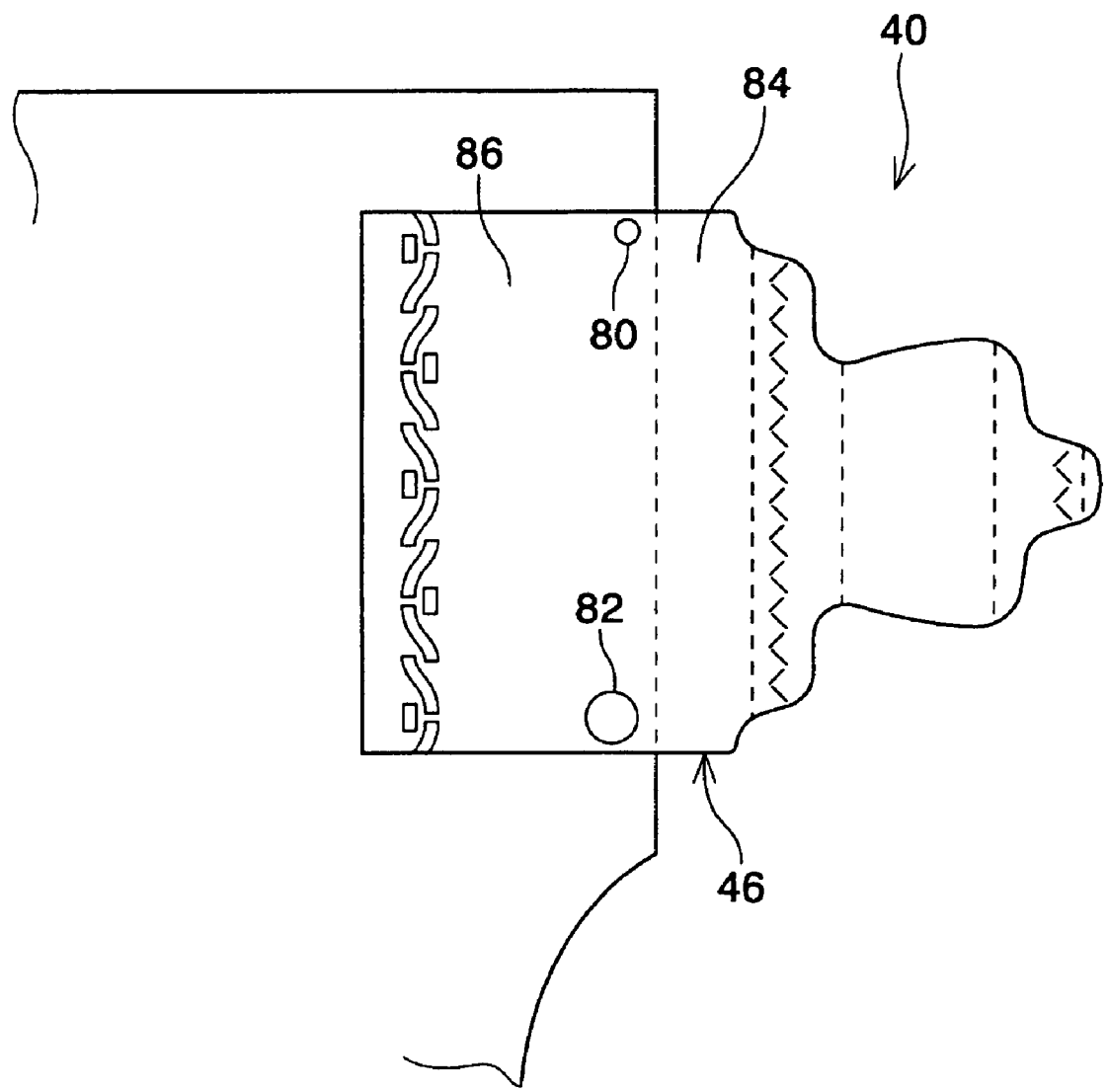
FIG. 9 is a second alternative embodiment of the stretchable fastening member with a restriction means.
Figure 10:
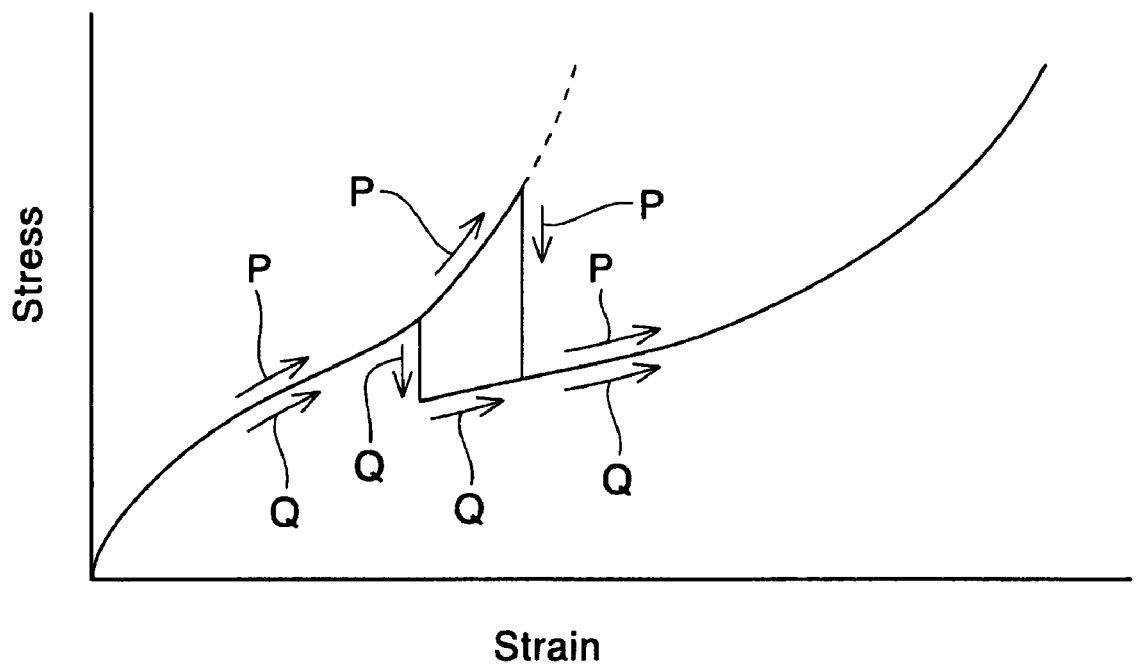
FIG. 10 is a graph showing the stress-strain curve of the stretchable fastening member shown in FIG. 9.

FIG. 9 also shows an alternative embodiment of a stretchable fastening member 40. The stretchable fastening member 40 shown in FIG. 9 comprises a restriction means comprising a waist restriction means 80 and a leg restriction means 82. The restriction means 80 and 82 may comprise a bonding means disposed generally in the longitudinal direction. The stretchable panel 46 comprises a first stretchable zone 84 and a second stretchable zone 86. The restriction means 80 and 82 virtually divides the stretchable panel 46 into the first stretchable zone 84 and the second stretchable zone 86 at a line connecting the restriction means 80 and 82. The bonding strength of the waist restriction means is different from the bonding strength of the leg restriction means. In the embodiment shown in FIG. 9, the bonding site of the leg restriction means 82 is bigger than the bonding site of the leg restriction means 80. Therefore, the leg restriction means 80 is capable of withstanding the applied extension force higher than the waist restriction means 80. As shown in FIG. 10, the leg side of stretchable panel 46 follows a path indicated by the arrow P and the waist side of the stretchable panel 46 follows a path indicated by the arrow Q. Alternatively, the bonding site of the waist restriction means may be bigger than the bonding site of the leg restriction means such that the waist restriction means is capable of withstanding the applied extension force higher than the leg restriction means.

Figure 11:
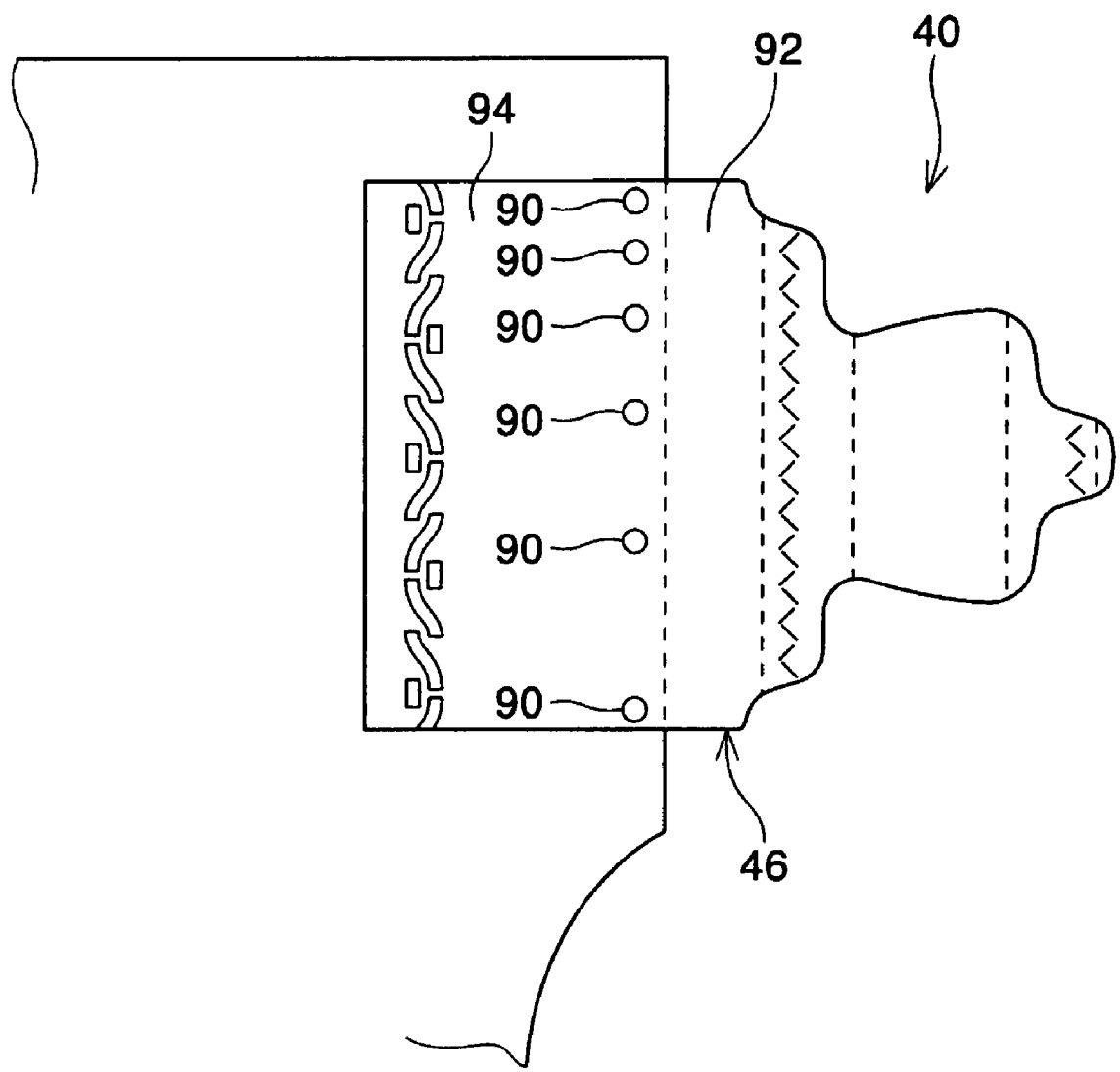
FIG. 11 is a third alternative embodiment of the stretchable fastening member with a restriction means.

FIG. 11 shows an alternative embodiment of a stretchable fastening member 40. The stretchable fastening member 40 shown in FIG. 11 comprises a plurality of restriction means 90 disposed generally in the longitudinal direction. The stretchable panel 46 comprises a first stretchable zone 92 and a second stretchable zone 94. The restriction means 90 virtually divides the stretchable panel 46 into the first stretchable zone 92 and the second stretchable zone 94 at a line connecting a plurality of restriction means 90. In FIG. 11, each restriction means is disposed such that each longitudinal interval between the adjacent restriction means is different. In the embodiment in shown in FIG. 11, the interval is smaller at the waist side of the stretchable panel 46 than at the leg side of the stretchable panel 46. Alternatively, the interval may be bigger at the waist side of the stretchable panel 46 than at the leg side of the stretchable panel 46

Figure 12:
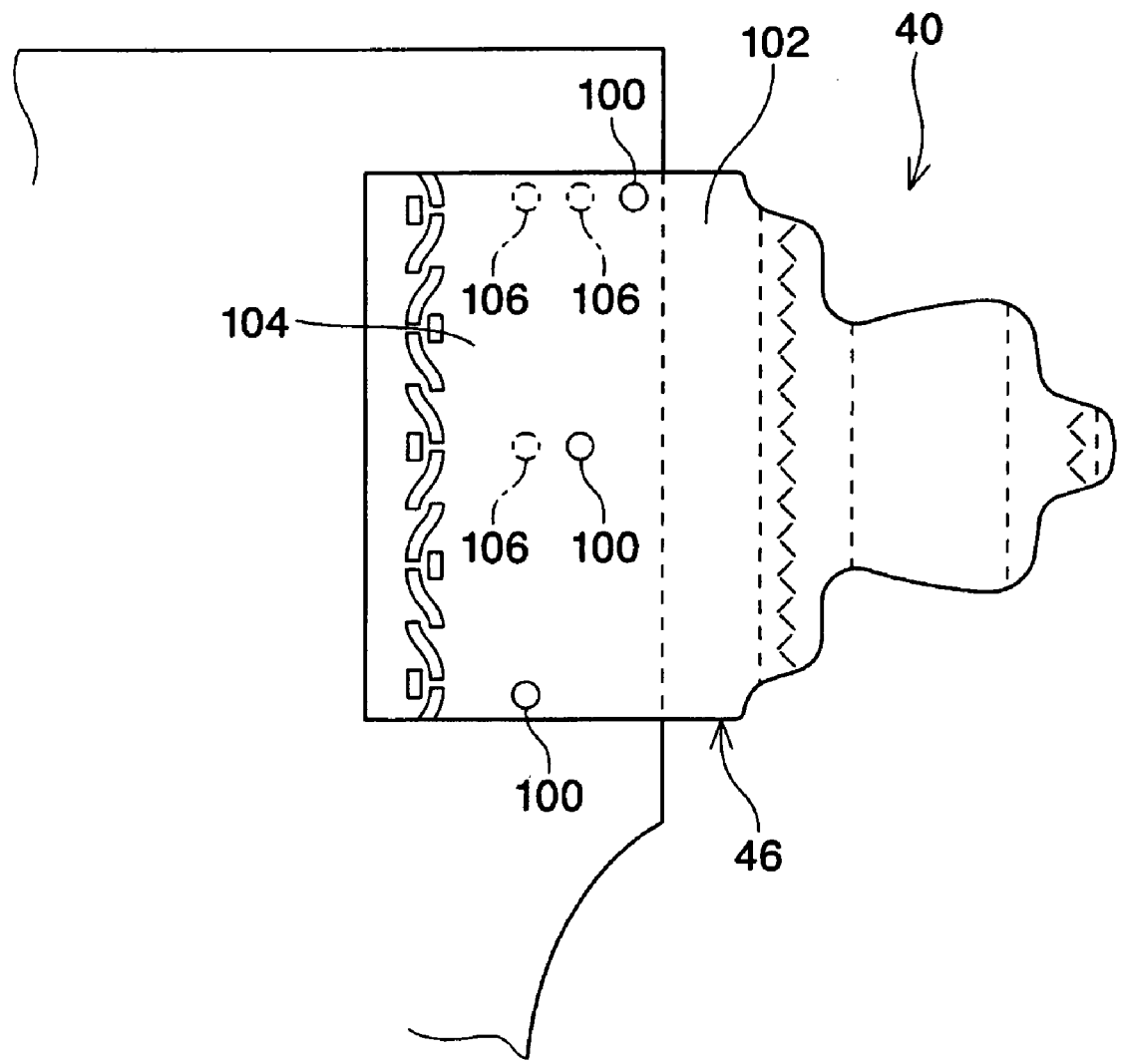
FIG. 12 is a fourth alternative embodiment of the stretchable fastening member with a restriction means.
Figure 13:
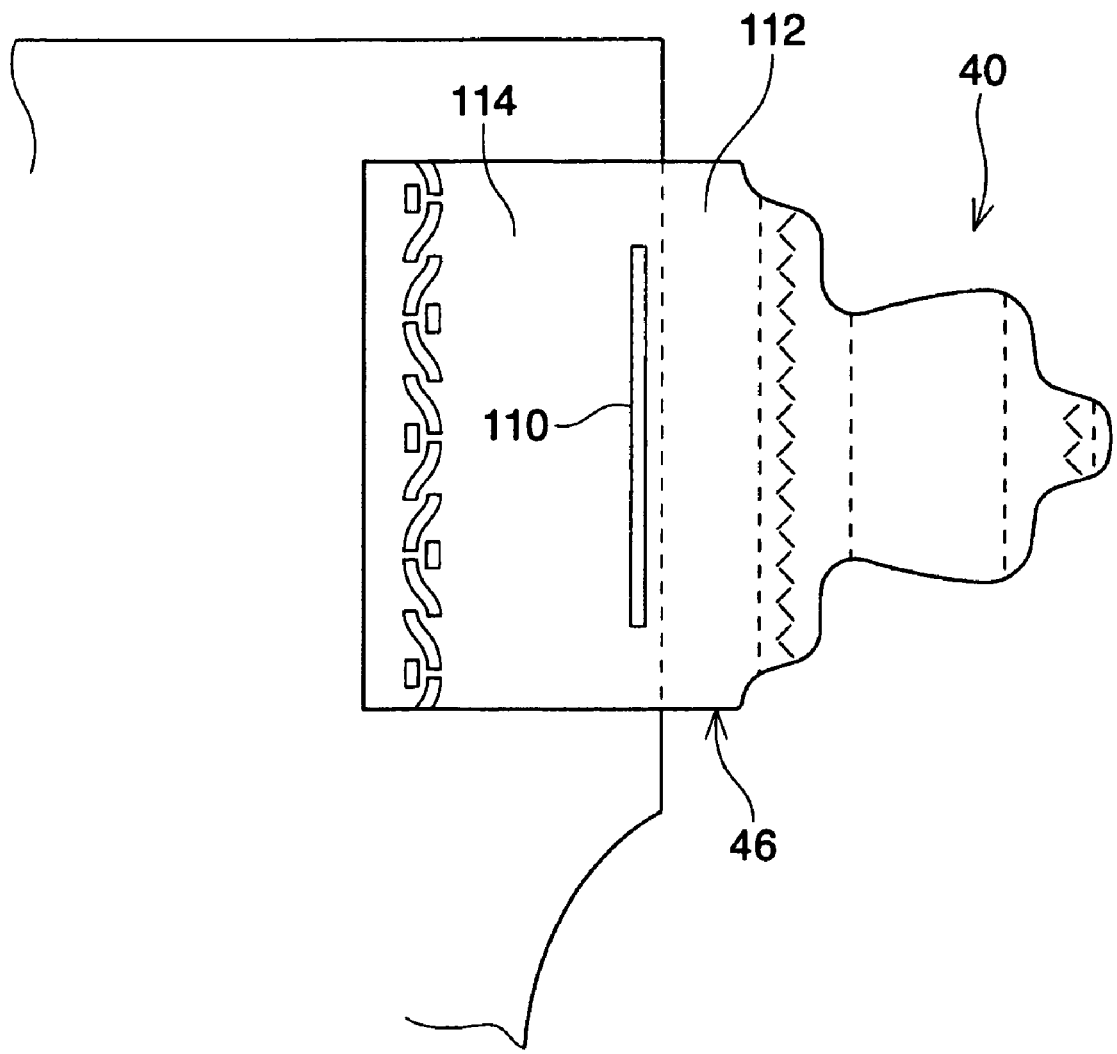
FIG. 13 is a fifth alternative embodiment of the stretchable fastening member with a restriction means.

FIG. 12 shows an alternative embodiment of a stretchable fastening member 40. The stretchable fastening member 40 shown in FIG. 12 comprises three restriction means 100 such that a line connecting the three restriction means 100 are disposed at an angle with the longitudinal direction. The stretchable panel 46 comprises a first stretchable zone 102 and a second stretchable zone 104. The restriction means 100 virtually divides the stretchable panel 46 into the first stretchable zone 102 and the second stretchable zone 104 at a line connecting the three restriction means 100. If necessary, additional restriction means 106 may be added in the second stretchable zone 102. FIG. 13 shows an alternative embodiment of a stretchable fastening member 40. The stretchable fastening member 40 shown in FIG. 13 comprises a restriction means 110 having a line shape. In the embodiment, the line shape restriction means 110 is disposed in the longitudinal direction. The stretchable panel 46 comprises a first stretchable zone 112 and a second stretchable zone 114. The restriction means 110 virtually divides the stretchable panel 46 into the first stretchable zone 112 and the second stretchable zone 114 at a line connecting the two restriction means 110. The restriction means 110 may comprise two or more line shape restriction means divided in the longitudinal direction.

What is claimed is:

1. An absorbent article comprising a chassis and a stretchable fastening member, the chassis extending longitudinally and laterally and comprising a liquid pervious topsheet, a liquid impervious backsheet and an absorbent core disposed therebetween, the stretchable fastening member comprising a fixed portion permanently joined to the chassis, a distal portion provided with a fastening material and a stretchable panel positioned between the fixed portion and the distal portion, the stretchable fastening member being joined to the chassis such that the distal portion is positioned laterally outwardly from the fixed portion in the flat-out configuration of the stretchable fastening member, wherein the stretchable panel comprises a laminate of a stretchable film and a nonwoven web, and wherein the stretchable panel of the stretchable fastening member comprises a first stretchable zone and a second stretchable zone disposed in the lateral direction, the first stretchable zone is capable of providing extensibility upon an initially applied extension force, and extensibility of the second stretchable zone is restricted by a restriction means until the restriction means is inactivated, and the restriction means is inactivated upon a further applied extension force such that the second stretchable zone provides an additional extensibility to reduce a stress developed in the stretchable panel.

2. The absorbent article of claim 1 wherein the restriction means is inactivated upon the applied extension force being not more than 350 g/25 mm.

3. The absorbent article of claim 1 wherein the chassis comprises a side flap being less stretchable than the stretchable panel, and at least a portion of the stretchable panel is superposed on the side flap of the chassis wherein, the restriction means comprises a bonding means to detachably join a portion of the stretchable panel to the side flap of the chassis between the fixed portion and the distal portion to provide the first stretchable zone extending between the distal portion and the bonding means and the second stretchable zone extending between the fixed portion and the bonding means.

4. The absorbent article of claim 3 wherein the bonding means is provided in the configuration where the stretchable panel is unfolded.

5. The absorbent article of claim 3 wherein the side flap of the chassis is non-stretchable.

6. The absorbent article of claim 3 wherein the bonding means is detached upon the applied extension force being not more than 350 g/25 mm.

7. The absorbent article of claim 3 wherein the bonding means comprises a waist bonding means and a leg bonding means.

8. The absorbent article of claim 7 wherein the bonding strength of the waist bonding means is different from the bonding strength of the leg bonding means.

* * * * *